(12) United States Patent
Rübben

(10) Patent No.: US 8,679,571 B2
(45) Date of Patent: Mar. 25, 2014

(54) METHOD FOR PRODUCING A BIOACTIVE SURFACE ON AN ENDOPROSTHESIS OR ON THE BALLOON OF A BALLOON CATHETER

(76) Inventor: Alexander Rübben, Monaco (MC)

( * ) Notice: Subject to any disclaimer, the term of this patent is extended or adjusted under 35 U.S.C. 154(b) by 307 days.

(21) Appl. No.: 12/936,952

(22) PCT Filed: Apr. 9, 2008

(86) PCT No.: PCT/EP2008/002960
§ 371 (c)(1),
(2), (4) Date: Jan. 2, 2011

(87) PCT Pub. No.: WO2009/124570
PCT Pub. Date: Oct. 15, 2009

(65) Prior Publication Data
US 2011/0092900 A1    Apr. 21, 2011

(51) Int. Cl.
*A61M 25/10* (2013.01)
*B05D 3/10* (2006.01)
(52) U.S. Cl.
USPC ........... 427/2.28; 427/2.24; 427/2.1; 604/509
(58) Field of Classification Search
USPC ...................................... 427/2.28, 2.24, 2.25
See application file for complete search history.

(56) References Cited

U.S. PATENT DOCUMENTS

| 5,102,402 | A |  | 4/1992 | Dror |  |
|---|---|---|---|---|---|
| 6,129,705 | A |  | 10/2000 | Grantz |  |
| 7,811,622 | B2 | * | 10/2010 | Bates et al. | 427/2.1 |
| 2004/0170752 | A1 | * | 9/2004 | Luthra et al. | 427/2.24 |
| 2005/0163914 | A1 | * | 7/2005 | Klee et al. | 427/2.24 |
| 2008/0021385 | A1 | * | 1/2008 | Barry et al. | 604/103.02 |

FOREIGN PATENT DOCUMENTS

| WO | 93/06881 |  | 4/1993 |
| WO | 0152915 | A | 7/2001 |
| WO | 02055122 | A | 7/2002 |
| WO | 2006032904 | A | 3/2006 |
| WO | 2007/030512 | A1 | 3/2007 |

\* cited by examiner

*Primary Examiner* — Cachet Sellman
(74) *Attorney, Agent, or Firm* — Gudrun E. Huckett

(57) ABSTRACT

A method for producing a bioactive surface on an endoprosthesis, or on the balloon (3) of a balloon catheter (1) is described, wherein the surface (15) of the endoprosthesis, or the surface (4) of the balloon (3) is softened. The surface (15) of the endoprosthesis, or the surface (4) of the balloon (3) is moistened with a solution (6) of an active ingredient (7), and the solvent (8) is separated from the active ingredient (7). In addition, a balloon (3) of a balloon catheter (1) is disclosed, which comprises an uncoated surface (4), wherein an unencapsulated active ingredient (7) is embedded at least partially into the material of the surface (4). Furthermore, a balloon catheter (1) is described, which comprises a balloon (3) according to the invention. In addition, an endoprosthesis, particularly a polymer stent is described, which comprises an uncoated surface (15), wherein an active ingredient (7) is embedded at least partially into the material of the surface (15).

13 Claims, 3 Drawing Sheets

METHOD FOR PRODUCING A BIOACTIVE SURFACE ON AN ENDOPROSTHESIS OR ON THE BALLOON OF A BALLOON CATHETER

BACKGROUND OF THE INVENTION

The present invention concerns a method for generating a bioactive surface on an endoprosthesis or on the balloon of a balloon catheter. The invention concerns moreover a balloon of a balloon catheter and a balloon catheter.

The so-called "minimally invasive methods" in medicine gain increasingly in significance. In the context of radiology in this connection interventional radiology is to be mentioned that has contributed significantly to the development of minimally invasive techniques and the devices and prostheses of suitable material required for this purpose. For example, today small metal screens as vessel endoprostheses, so-called stents, are inserted by cardiologists as well as radiologists into vessels in order to keep them open. In connection with conventional stents, there is however often a thickening of the vessel wall with consecutive lumen constriction in the area of the stent by cell proliferation or by deposits of cells. Moreover, balloon catheters are inserted by cardiologists as well as radiologists in vessels in order to open them. In connection with these surgical procedures, there is also a thickening of the vessel wall with consecutive lumen construction in the area of the expansion by cell proliferation.

By medication release from the surface of the endoprosthesis or from the surface of the balloon of the balloon catheter, which surface may be provided for improvement of medicament loading and medicament release with a suitable polymer coating, this problem can be counteracted. Typically, an active ingredient that is dissolved in a solvent is applied to the surface of the endoprosthesis or the surface of the balloon of the balloon catheter, and the solvent subsequently evaporates. The active ingredient is then located on the surface.

Possibilities for obtaining in comparison thereto an improved adhesion of the active ingredient on the surface, are disclosed in the documents U.S. Pat. No. 5,102,402 and U.S. Pat. No. 6,129,705. The document U.S. Pat. No. 5,102,402 discloses a balloon catheter coated with medicaments. In this connection, in a first variant microcapsules filled with an active ingredient or medicament are enclosed by folds in the balloon surface and in this way mechanically held in their respective position. In a second variant the microcapsules are glued by means of a bonding agent to the balloon surface. In the context of this document, uncoated active ingredient crystals are also viewed as microcapsules.

In the document U.S. Pat. No. 6,129,705 a balloon catheter and a stent are disclosed whose surfaces have each a coating in which microcapsules that are filled with an active ingredient are completely embedded. In one embodiment variant a balloon catheter is described having in its uncoated surface microcapsules filled with an active ingredient extruded during the manufacturing process. However, filling the active ingredient into microcapsules and the subsequent attachment or embedding of the microcapsules on the balloon surface or stent surface are comparatively complex and thus expensive methods.

It is therefore a first object of the present invention to provide an advantageous method for generating a bioactive surface on an endoprosthesis or on the balloon of a balloon catheter. It is a second object of the invention to provide an advantageous balloon of a balloon catheter. A third object resides in providing an advantageous balloon catheter. A fourth object resides in providing an advantageous endoprosthesis.

SUMMARY OF THE INVENTION

The first object is solved by a method wherein the surface of the endoprosthesis or the surface of the balloon is softened, the surface of the endoprosthesis or the surface of the balloon is wetted with a solution of an active ingredient; and the solvent is separated from the active ingredient, the second object by a balloon of a balloon catheter wherein an unencapsulated active ingredient is embedded at least partially into the material of the surface, the third object by a balloon catheter with a balloon having an unencapsulated active ingredient embedded at least partially into the material of the surface of the balloon, and the fourth object by an endoprosthesis wherein an active ingredient is embedded at least partially in the material of the surface. The dependent claims contain further advantageous embodiments of the invention. The features are advantageous individually as well as in combination.

In the method according to the invention for generating a bioactive surface on an endoprosthesis or on the balloon of a balloon catheter the surface of the endoprosthesis or the surface of the balloon is softened and is then wetted with a solution of active ingredient. Subsequently, the solvent is separated from the active ingredient.

This is a very simple and inexpensive method in which the active ingredient as a result of softening of the surface is embedded entirely or partially in the surface or adheres to the surface. In the context of the method according to the invention the principle of solution welding (solvent welding) is utilized. The method according to the invention effects in comparison to simple deposition of active ingredient on the surface an improved adhesion of the active ingredient on or in the surface. Moreover, in comparison to the methods disclosed in the documents U.S. Pat. No. 5,102,402 and U.S. Pat. No. 6,129,705, a significantly simpler and less expensive method is provided.

The surface of the endoprosthesis or the surface of the balloon can be softened in particular by means of a solvent, for example, by means of a solution of the active ingredient. As a solvent, for example, dimethyl sulfoxide (DMSO), dioxane, dimethyl formamide (DMF), tetrahydrofuran (THF), methylene chloride or chloroform can be used. These solvents are in particular miscible with water. Basically, the surface of the endoprothesis or the surface of the balloon can also be softened in other ways, for example, thermally.

In case that the surface of the endoprosthesis or the surface of the balloon is softened by means of the solvent of the active ingredient, the first two method steps, i.e., softening and wetting, can be performed simultaneously. The surface of the endoprosthesis or of the balloon can be wetted, for example, by immersion, spraying or pipetting with the solvent or with the solution of the active ingredient.

Advantageously, an endoprosthesis or a balloon can be used whose surface comprises a polymer. In particular, an endoprosthesis or a balloon can be used that is comprised of a polymer. It can be, for example, a balloon of nylon or a nylon Pebax mixture.

The employed active ingredient can be in particular tretinoin and/or tretinoin derivatives and/or orphan receptor agonists and/or elafin derivatives and/or corticosteroids and/or steroid hormones and/or paclitaxel and/or taxol and/or taxol derivatives and/or rapamune and/or tacrolimus and/or hydrophobic proteins and/or substances that change cell proliferation. As steroid hormones e.g. methyl prednisolone, dexamethasone or estradiol can be used.

Advantageously, excessive active ingredient and solvent can be removed by movement of the endoprosthesis or of the balloon, for example, by spinning or knocking, from the wetted surface. By movement of the endoprosthesis or the balloon, in particular, by spinning, a uniform distribution of the solvent and thus also of the active ingredient on the surface of the endoprosthesis or the balloon can be achieved. This prevents effectively a possible formation of lumps.

Moreover, the surface area of the endoprosthesis or of the balloon can be enlarged before softening. For example, the surface area of the endoprosthesis or the balloon can be mechanically, thermally or chemically enlarged. The surface area of the endoprosthesis or of the balloon can be in particular enlarged by structuring or profiling. For example, the surface of the endoprosthesis or of the balloon can be structured or profiled by roughening. Advantageously, by enlarging the surface area of the endoprosthesis or the balloon, depressions with a depth of 5-50 µl and a width of 5-50 µm are produced on the surface.

Moreover, the surface of the endoprosthesis or the surface of the balloon can be wetted with a solvent of an active ingredient in a solvent that is miscible with water wherein the active ingredient has a solubility of maximally 0.9 mg/ml in distilled water. In this case, the solvent can be separated from the active ingredient in that the wetted endoprosthesis or the wetted balloon is immersed in water. In this way, the active ingredient that is insoluble in water will precipitate and deposit partially on the surface of the endoprosthesis or the balloon. Since the surface of the endoprosthesis or of the balloon is softened, the active ingredient is entirely or partially embedded in the surface or adheres at least to the surface. As water-soluble solvents in particular the aforementioned solvents can be employed.

As an alternative to the afore described deposition of the active ingredient on the surface by precipitation, the solvent can also be separated from the active ingredient by evaporation of the solvent. In this case, water solubility of the solvent is not required.

Basically, the surface of the endoprosthesis or of the balloon can be functionally coated with a polymer layer before generating the bioactive surface. In this case, the thickness of the functional polymer layer is 10-1,000 µM, advantageously 200-400 µm. The surface of the endoprosthesis or of the balloon can be functionally coated before generating the bioactive surface, for example, with polyamino-p-xylylene-co-polyxylylene.

For producing a functional polymer layer, from the starting compounds of the general formulas (1), (2) and/or (3) at raised temperatures and reduced pressures monomers can be generated in the gas phase and by cooling can be polymerized at reduced temperatures, wherein:

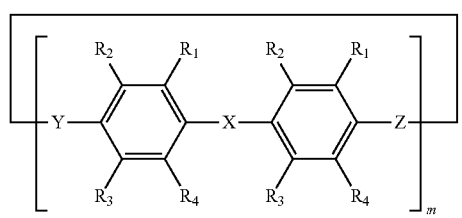

(1)

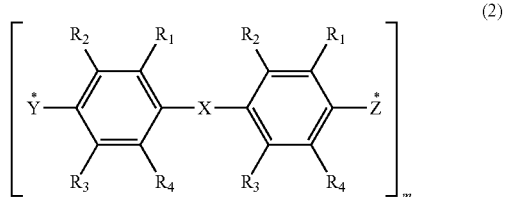

(2)

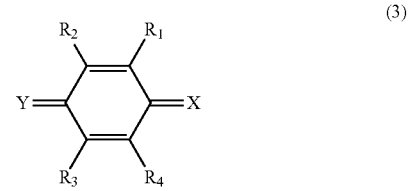

(3)

$R_{1,2,3,4}$: each being the same or different from each other, hydrogen atoms, halogen atoms, alkyl groups or substituted alkyl groups, aryl groups or substituted aryl groups, organic residues and radicals, groups of the general structure CO(O-M-A), metal-containing groups, hydroxyl groups, amino groups, carboxyl groups, ester groups, ether groups, acid halide groups, isocyanate groups, sulfur-containing groups, nitrogen-containing groups, phosphorus-containing groups, silicon-containing groups;
X, Y: hydrocarbon residues;
m: number of repeating units=1-20
wherein the required temperatures for producing the monomers are between 500° C. and 1,000° C. and the required pressures are smaller than 500 Pa. Dimers of the structure (1) or (2) with m=1 can be cleaved to monomers at temperatures between 600° C. and 900° C. and pressures smaller than 100 Pa, for example. The subsequent polymerization can then be performed at temperatures below 120° C.

Basically, in the context of the method according to the invention a stent can be employed as an endoprosthesis.

The balloon of a balloon catheter according to the invention comprises an uncoated surface. An unencapsulated active ingredient is at least partially is embedded into the material of the surface. The active ingredient can thus be embedded entirely or partially in the surface. In the case of only partial embedding, the active ingredient at least adheres on the surface. The material of the surface of the balloon can be in particular a polymer, for example, nylon or a nylon Pebax mixture. The balloon can also consist of nylon or a nylon Pebax mixture.

The active ingredient that is at least partially embedded in the surface may be tretinoin and/or tretinoin derivatives and/or orphan receptor agonists and/or elafin derivatives and/or corticosteroids and/or steroid hormones and/or paclitaxel and/or taxol and/or taxol derivatives and/or rapamune and/or tacrolimus and/or hydrophobic proteins and/or substances that change cell proliferation. The steroid hormones may be e.g. methyl prednisolone, dexamethasone or estradiol.

The balloon catheter according to the invention comprises a balloon according to the invention as it has been described above. The balloon according to the invention as well as the balloon catheter according to the invention have the advantage that they can be produced simply and expensively and moreover ensure a safe adhesion of the active ingredient on the surface as a result of the at least partial embedding thereof.

The endoprosthesis according to the invention comprises an uncoated surface. Into the material of the surface an active ingredient is embedded at least partially. The active ingredient can be embedded, of course, also completely into the material of the surface. The endoprosthesis can be in particular a stent, preferably a polymer stent. Basically, the material of the surface can comprise a polymer. The active ingredient that is at least partially embedded in the surface area can be tretinoin and/or tretinoin derivatives and/or orphan receptor agonists and/or elafin derivatives and/or corticosteroids and/or steroid hormones and/or paclitaxel and/or taxol and/or taxol derivatives and/or rapamune and/or tacrolimus and/or hydrophobic proteins and/or substances that change cell proliferation. The steroid hormones may be e.g. methyl prednisolone, dexamethasone or estradiol. The endoprosthesis according to the invention has the same advantages as the balloon of the balloon catheter according to the invention.

BRIEF DESCRIPTION OF THE DRAWINGS

Further features, properties and advantages of the present invention are described in the following based on embodiments with reference to the attached Figures. The features are advantageous individually as well as in combination with each other.

DESCRIPTION OF PREFERRED EMBODIMENTS

Figure 1:
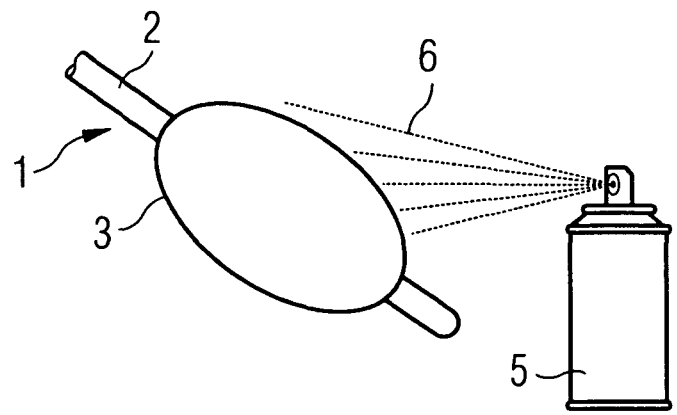
FIG. 1 shows schematically a balloon catheter that is sprayed with a solution of the active ingredient.

A first embodiment of the present invention will be explained in the following with the aid of the FIGS. 1 to 6 in more detail. FIG. 1 shows schematically a balloon catheter 1 that by means of a spraying device 5 is sprayed with the solution 6 of an active ingredient 7 in a solvent 8 that is miscible with water. The balloon catheter 1 comprises a catheter probe 2 and a balloon 3. The balloon 3 surrounds a portion of the catheter probe 2. The balloon 3 is comprised of a polymer, for example, nylon or a nylon Pebax mixture. The surface of the balloon 3 is wetted by means of a spraying device 5 with a solution 6 of an active ingredient 7 in a solvent 8 that is miscible with water and in this way is wetted. In place of the spraying action the balloon 3 of the balloon catheter 1 can also be immersed in a solution of an active ingredient in a solvent that is miscible with water or can be pipetted with it. The solvent 8 has the effect that the surface of the balloon 3 is softened.

Basically, the surface of the balloon 3 can also be softened first, for example, by means of a softening agent, and subsequently can be wetted with a solution of an active ingredient 6.

Figure 2:
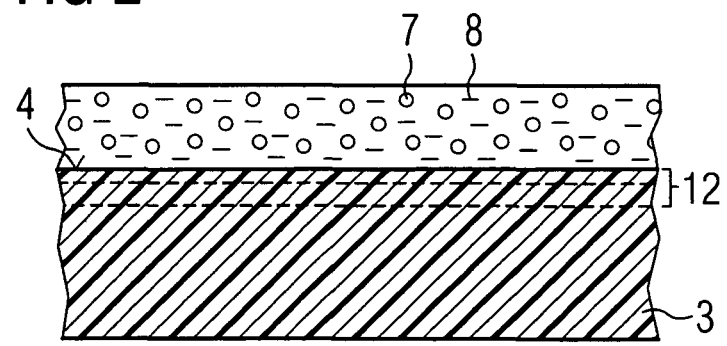
FIG. 2 shows schematically a section of a part of the surface of the balloon of a balloon catheter having on its softened surface the solution of an active ingredient.

FIG. 2 shows schematically a section of a part of the surface of the balloon 3 of the balloon catheter 1 whose surface is wetted with the solution of an active ingredient 7. The area of the surface 4 that is softened by the solvent 8 is referenced by reference numeral 12. On the softened surface 4 of the balloon 3 there is a mixture of a solvent 8 and an active ingredient 7.

The employed active ingredient 7 can be, for example, tretinoin and/or tretinoin derivatives and/or orphan receptor agonists and/or elafin derivatives and/or corticosteroids and/or steroid hormones and/or paclitaxel and/or taxol and/or taxol derivatives and/or rapamune and/or tacrolimus and/or hydrophobic proteins and/or substances that change cell proliferation, wherein as steroid hormones methyl prednisolone, dexamethasone or estradiol can be used. The solvent 8 can be, for example, dimethyl sulfoxide (DMSO), dioxane, dimethyl formamide (DMF), tetrahydrofuran (THF), methylene chloride or chloroform.

Figure 3:
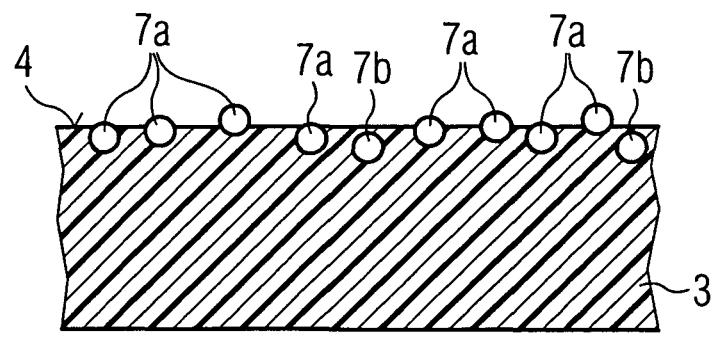
FIG. 3 shows schematically a section of a part of the surface of the balloon of a balloon catheter having an active ingredient embedded in its surface.

After wetting the surface 4, the solvent is evaporated or allowed to evaporate. During this time the active ingredient 7 in its entirety or partially is embedded into the softened surface 4. This is indicated schematically in FIG. 3. FIG. 3 shows a section of a part of surface 4 of a balloon 3 of balloon catheter 1 having embedded in its surface 4 an active ingredient 7a, 7b. The active ingredient that is partially embedded in the surface 4 is referenced by reference numeral 7a and the active ingredient that is embedded completely into the surface 4 is referenced by reference numeral 7b.

A second embodiment variant of the first embodiment is explained in more detail in the following with the aid of FIGS. 4 and 5. In this embodiment variant the balloon 3 is first softened, as described in connection with FIGS. 1 and 2, and is wetted with a solution of an active ingredient 6. Subsequently, in contrast to the afore described embodiment variant, the solvent 8 is not evaporated but the active ingredient 7 is deposited by precipitation on the softened surface 4.

Figure 4:
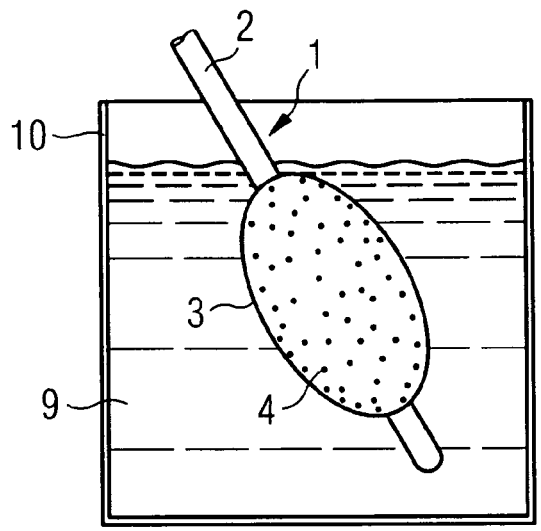
FIG. 4 shows schematically the immersion of a balloon catheter, wetted with the solution of an active ingredient, in a water bath.

FIG. 4 shows schematically the immersion of the balloon catheter wetted with the solution of an active ingredient 6 in a water bath. In FIG. 4, a vessel 10 is illustrated that is filled with water 9. The balloon 3 of the balloon catheter 1 is completely immersed in the water 9. The softened and wetted surface 4 of the balloon 3 is in direct contact with the water 9.

Figure 5:
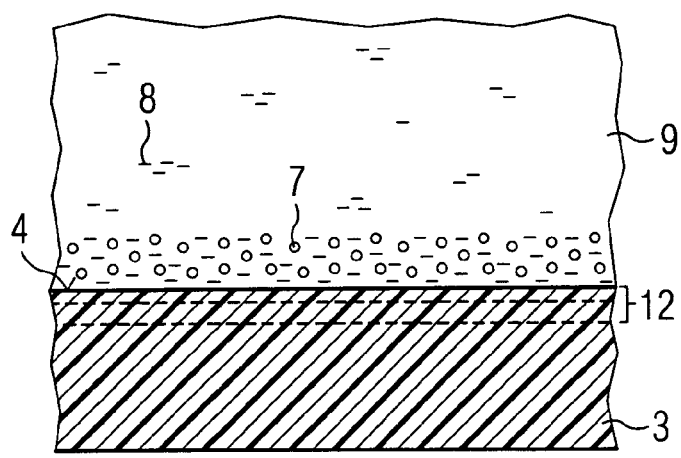
FIG. 5 shows schematically a section of a part of the softened surface of the balloon of the balloon catheter that is located in water.

FIG. 5 shows schematically a section of a part of the softened surface 4 of the balloon 3 of catheter of the balloon catheter 1 which is located in water 9. As a result of the direct contact between the water 9 and the solvent 8 that is miscible with water an increasing mixing of the solvent 8 with water 9 takes place. This is schematically indicated in FIG. 5. The active ingredient 7 that is insoluble in water or at least only soluble with difficulty in water will precipitates, on the other hand, on the softened surface 4 of the balloon 3 and is embedded therein, as disclosed in connection with FIG. 3. In this way, the active ingredient 7 is separated from the solvent 8.

After the active ingredient 7 has precipitated on the surface 4 the balloon 3 of the balloon catheter 1 can be removed from the water bath. The water that may still be present on the surface 4 of the balloon 3 may subsequently be allowed to evaporate. However, as a result of embedding of the active ingredient 7 in the surface 4, the active ingredient 7 is already fixedly connected to the surface 4 of the balloon 3 so that the balloon 3 in principle must not be dried i.e., may remain wet.

Subsequently, a third embodiment variant of the first embodiment will be explained in more detail with the aid of FIG. 6. In this embodiment variant the surface 4 of the balloon 3 is first roughened before being softened. This can be done in particular mechanically, chemically, or thermally. In this connection, on the surface 4 of the balloon 3 in particular depressions with a depth of 5-50 µm and width of 5-50 µm can be generated.

Subsequently, the roughened surface 13 of the balloon 3, as disclosed in the first two embodiment variants, can the softened and wetted with the solution of an active ingredient 6. After the solvent 8 has been separated, for example, by allowing it to evaporate or by precipitation, from the active ingredient 7, the active ingredient is embedded entirely or partially in the roughened surface 13 of the balloon 3. This is schematically indicated in FIG. 6.

Figure 6:
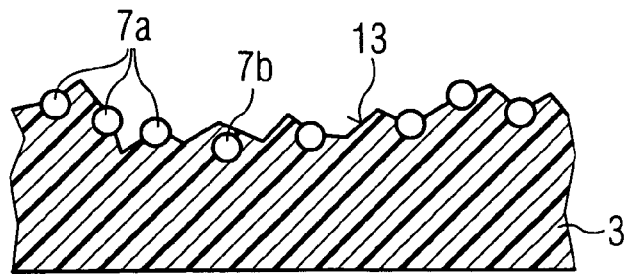
FIG. 6 shows schematically a section of a part of the surface of a balloon of a balloon catheter having embedded on its roughened surface an active ingredient.

FIG. 6 shows schematically a section of a part of the surface 13 of a balloon 3 of a balloon catheter 1 having embedded in its roughened surface 13 the active ingredient 7. The active ingredient embedded partially in the surface 13 is referenced with reference numeral 7a, the completely embedded active ingredient is referenced with reference numeral 7b.

In the following, a second embodiment will be explained with the aid of FIGS. 7 to 10 in more detail. Elements that correspond to such elements that have already been explained in connection with the first embodiment are identified with the same reference numerals and are not described again in detail. The instant embodiment relates to a stent that is coated with an active ingredient 7. In this connection, the stent is a polymer stent.

Figure 7:
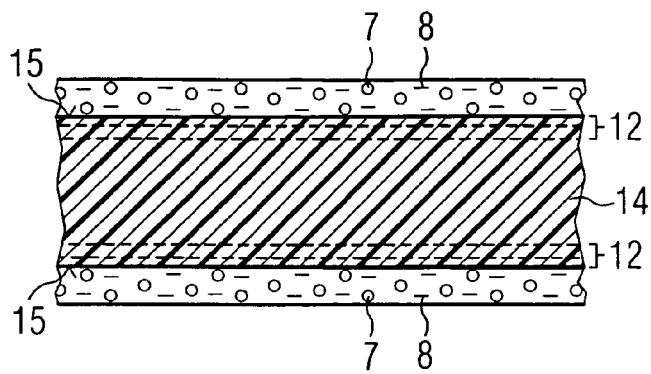
FIG. 7 shows schematically the section of a part of a screen structure of a stent whose surface is softened and is wetted with a solution of an active ingredient.

FIG. 7 shows schematically a section of a part of a screen structure 14 of a stent whose surface 15 is softened and wetted with a solution of an active ingredient as described in connection with FIG. 1. The softened part of the surface 15 of the screen structure 14 is referenced with reference numeral 12. As a solvent 8 or active ingredient 7 the substances mentioned in connection with the first embodiment can be employed. Subsequently, the solvent 8 is separated either by allowing it to evaporate or by precipitation from the active ingredient 7 wherein the active ingredient 7 becomes embedded in the surface of the screen structure 14. With respect to details in this regard reference is being had to the embodiment variants of the first embodiment.

Figure 8:
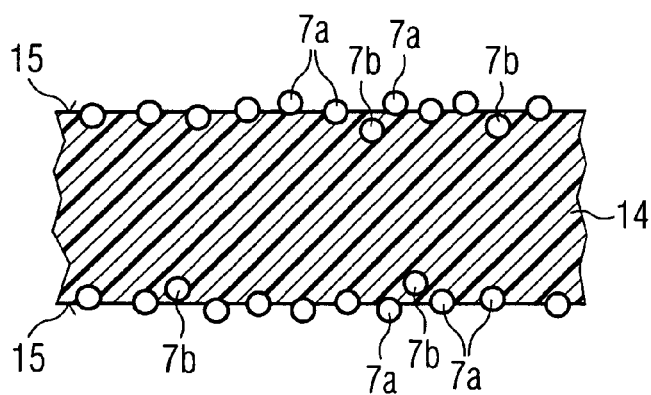
FIG. 8 shows schematically the section of a part of a screen structure of a stent having embedded in its surface an active ingredient.

FIG. 8 shows schematically a section of a part of a screen structure 14 of a stent having embedded in its surface 15 an active ingredient 7. The active ingredient that is partially embedded in the surface 15 is referenced by reference numeral 7a, the completely embedded active ingredient is referenced by reference numeral 7b.

In the following, a second embodiment variant of the second embodiment is described in more detail in connection with FIGS. 9 and 10. In contrast to the afore described embodiment variant the stent 14, which in this case must not be a polymer stent, is first functionally coated with a polymer layer 16. For this purpose, for example on the stent 14 the dimeric 4-amino-[2,2]-paracyclophane is cleaved at 700° C. and 20 Pa into reactive monomers and polymerizes subsequently on the surface of the stent 14 that is cooled to approximately 20° C. The desired thickness of the polymer coating is advantageously 10-1,000 µm, even more advantageous 200-400 µm.

The thus generated polymer layer 16 can now either be softened and wetted directly with a solution 6 of an active ingredient 7 in a solvent 8 that is miscible with water, as disclosed in the first embodiment in connection with FIG. 1. In addition, the surface area of the polymer coating 16 can be enlarged prior to softening and wetting, for example, by roughening. The possibilities for enlarging the surface area of the balloon 3 disclosed in detail in the first embodiment are also suitable for a possible enlargement of the surface area of the polymer coating 16 in the present embodiment. The roughened surface of the polymer coating 16 is subsequently, as disclosed in connection with the first embodiment, wetted with a solution 6 of an active ingredient 7 in a solvent 8 miscible with water and softened at the same time.

Figure 9:
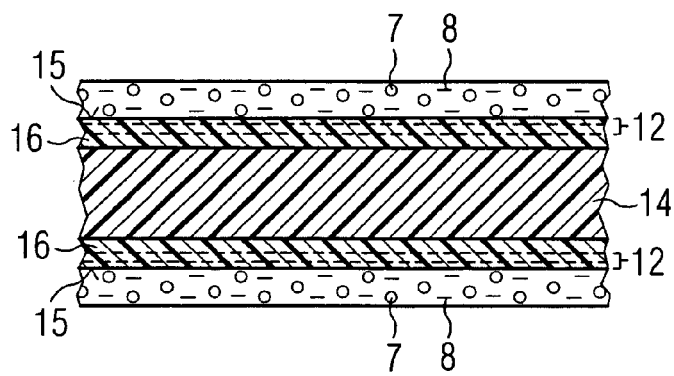
FIG. 9 shows schematically the section of a part of a screen structure of a stent that was functionally coated with a polymer and that has on its softened polymer surface a solution of an active ingredient.

FIG. 9 shows schematically a section of a part of a screen structure 14 of a stent that was coated with a polymer 16 and that has on its softened polymer surface the solution of the active ingredient 7. The softened area of the polymer coating 16 is referenced with the reference numeral 12. As a solvent 8 or active ingredient 7 the substances that have been mentioned in the first embodiment can be employed.

The solvent 8 that is located on the softened and wetted surface of the polymer coating 16 can be selectively allowed to evaporate or the stent, as explained in the first embodiment in connection with FIGS. 4 and 5 based on the example of the balloon 3, can be immersed in a water bath whereupon the active ingredient 7 will precipitate on the polymer-coated surface and will be embedded therein.

In case of evaporation, in all described embodiments and embodiment variants the use of a solvent that is immiscible with water or only soluble with difficulty in water is possible also.

Figure 10:
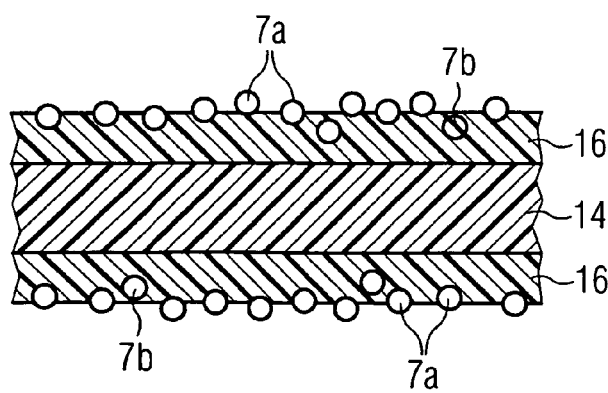
FIG. 10 shows schematically the section of a part of a screen structure of a stent that is functionally coated with a polymer and has embedded in its polymer surface an active ingredient.

Embedding of the active ingredient 7 in the polymer coating 16 obtained in the described way is schematically illustrated in FIG. 10. FIG. 10 schematically shows a section of a part of a screen structure 14 of a stent that is coated functionally with a polymer 16 and that has embedded in its polymer coating 16 an active ingredient 7. The active ingredient embedded partially in the polymer coating 16 is referenced by reference numeral 7a, the completely embedded active ingredient is referenced by reference numeral 7b.

What is claimed is:

1. A method for producing a bioactive surface on an uncoated surface of a balloon of a balloon catheter, wherein the surface of the balloon comprises a polymer, the method comprising the steps of:
    wetting the uncoated surface of the balloon with a solution of an active ingredient in a water-miscible solvent and softening the uncoated surface of the balloon with the solution of the active ingredient;
    immersing in water the uncoated surface of the balloon wetted with the solution of the active ingredient and precipitating, and at least partially embedding, the active ingredient, having a solubility of maximally 0.9 mg/ml in distilled water, in the uncoated surface of the balloon.

2. The method according to claim 1, wherein the solvent is dimethyl sulfoxide (DMSO), dioxane, dimethyl formamide (DMF), tetrahydrofuran (THF), methylene chloride or chloroform.

3. The method according to claim 1, wherein the balloon consists of a polymer.

4. The method according to claim 3, wherein the balloon consists of nylon or of a nylon Pebax mixture.

5. The method according to claim 1, wherein in the step of immersing in water the solvent of the solution of the active ingredient is separated from the active ingredient.

6. The method according to claim 1, wherein the active ingredient is selected from the group consisting of tretinoin, tretinoin derivatives, orphan receptor agonists, elafin derivatives, corticosteroids, steroid hormones, paclitaxel, taxol, taxol derivatives, rapamune, tacrolimus, hydrophobic proteins, and substances that change cell proliferation.

7. The method according to claim 6, wherein the steroid hormones are selected from methyl prednisolone, dexamethasone and estradiol.

8. The method according to claim 6, wherein a surface area of the balloon is enlarged before wetting and softening.

9. The method according to claim 8, wherein the surface area is mechanically, thermally, or chemically enlarged.

10. The method according to claim 1, comprising the step of enlarging a surface area of the balloon by structuring or profiling before the step of wetting and softening.

11. The method according to claim 10, wherein structuring or profiling is carried out by roughening.

12. The method according to claim 10, wherein the step of enlarging the surface area generates depressions with a depth of 5-50 micrometers and a width of 5-50 micrometers on the surface of the balloon.

13. A balloon of a balloon catheter that comprises a bioactive surface prepared according to claim 1.

* * * * *